United States Patent
Liaw

(10) Patent No.: US 7,763,691 B2
(45) Date of Patent: Jul. 27, 2010

(54) NORBORNENE MONOMERS WITH FLUORENE GROUP AND POLYMER MATERIAL THEREOF

(75) Inventor: Der-Jang Liaw, Taipei (TW)

(73) Assignee: National Taiwan University of Science & Technology, Taipei (TW)

( * ) Notice: Subject to any disclaimer, the term of this patent is extended or adjusted under 35 U.S.C. 154(b) by 0 days.

(21) Appl. No.: 11/905,939

(22) Filed: Oct. 5, 2007

(65) Prior Publication Data

US 2009/0023877 A1   Jan. 22, 2009

(30) Foreign Application Priority Data

Jul. 19, 2007  (TW) .............................. 96126323 A

(51) Int. Cl.
  *C08F 12/06*   (2006.01)
  *C08F 12/26*   (2006.01)
  *C08F 10/14*   (2006.01)
  *C08G 61/00*   (2006.01)

(52) U.S. Cl. ...................... 526/281; 525/55; 525/326.1; 525/329.5; 525/374; 525/418; 526/90; 526/170; 526/171; 526/172; 526/183; 526/193; 526/201; 526/221; 526/258; 526/259; 526/260; 526/280; 526/310; 526/319; 526/330; 528/9; 528/395; 528/398; 528/423; 540/450; 540/476; 540/479; 548/400; 548/416; 548/427; 548/436; 548/439; 548/440; 548/445; 548/528; 560/8; 560/101; 560/102

(58) Field of Classification Search ................ 526/280, 526/281, 258, 259, 260, 193, 221, 90, 172; 532/16, 136

See application file for complete search history.

(56) References Cited

U.S. PATENT DOCUMENTS

| | | | | |
|---|---|---|---|---|
| 4,080,491 | A * | 3/1978 | Kobayashi et al. | 526/137 |
| 7,205,359 | B2 * | 4/2007 | Liaw et al. | 525/288 |
| 7,271,230 | B2 * | 9/2007 | Liaw et al. | 526/259 |
| 7,323,518 | B2 * | 1/2008 | Liaw et al. | 525/301 |
| 7,335,704 | B2 * | 2/2008 | Liaw et al. | 525/279 |

(Continued)

FOREIGN PATENT DOCUMENTS

KR   2005058879 A  *  6/2005

OTHER PUBLICATIONS

Marder et al., "Synthesis of acrylate and norbornene polymers with pendant 2,7-bis(diarylamino)fluorene hole-transport groups", Tetrahedron 2004, 60(34), 7169-7176.*

(Continued)

*Primary Examiner*—Vasu Jagannathan
*Assistant Examiner*—Richard A Huhn
(74) *Attorney, Agent, or Firm*—Muncy, Geissler, Olds & Lowe, PLLC

(57) ABSTRACT

Norbornene monomers with fluorene group and polymer material thereof are disclosed. The norbornene monomers with fluorene group are prepared by Diels-Alder reation. The Norbornene monomers containing fluorene groups are highly active for ring-opening-metathesis polymerization (ROMP), and the molecular weight and PDI value of the obtained polymers are controllable.

5 Claims, 3 Drawing Sheets

U.S. PATENT DOCUMENTS

| | | | |
|---|---|---|---|
| 7,388,055 B2* | 6/2008 | Liaw et al. | 525/279 |
| 2005/0182218 A1* | 8/2005 | Liaw et al. | 526/258 |
| 2005/0182220 A1* | 8/2005 | Liaw et al. | 526/282 |

OTHER PUBLICATIONS

Weck et al., "Norbornene-Based Copolymers with Iridium Complexes and Bis(carbazolyl)fluorene Groups in Their Side-Chains and Their Use in Light-Emitting Diodes", Chem. Mater. 2007, 19(23), 5602-5608.*

Liaw et al., "Preparation of New Diblock Polymeric Materials With Carbazole Groups Derived from the Combination of Living Ring-Opening Metathesis Polymerization and Atom Transfer Radical Polymerization", Polymer Preprints 2003, 44(1), 945-946.*

Zaami et al., "Blue Light Emission from a Fluorene-Carbazole-Fluorene Trimer Incorporated as the Side Chain into a Polynorbornene", Macromol. Chem. Phys. 2004, 205(4), 523-529.*

Lai et al., "Ring-Opening Metathesis Polymerization of New Norbornene-Based Monomers Containing Various Chromophores", J. of Polym. Sci. Part A. Polym. Chem. 2007, 45(14), 3022-3031.*

Advincula et al., "Synthesis and Oxidative Cross-Linking of Fluorene-Containing Polymers To Form Conjugated Network Polyfluorenes: Poly(fluoren-9,9-diyl-alt-alkan-alpha,omega-diyl)", Macromol. 2002, 35, 2426-2428.*

* cited by examiner

NORBORNENE MONOMERS WITH FLUORENE GROUP AND POLYMER MATERIAL THEREOF

BACKGROUND OF THE INVENTION

1. Field of the Invention

The present invention relates to norbornene monomers and polymer material thereof and, more particularly, to norbornene monomers with fluorene group and polymer material thereof.

2. Description of the Related Art

Polynorbornene and its derivative were the first commercial products produced from ring-opening metathesis polymerization (ROMP) and were important elastomers. Due to high transparency, improved impact resistance, wide temperature range usage and good mechanical and processing properties, polynorbornene and their derivatives are widely applied in shape-memory polymers, lighting devices, machines, electric components, pipe fittings and food packaging.

Previously metathesis polymerization of olefins was an important process for polymerization, especially the cycloolefin ring-opening metathesis polymerization and non-cyclic diene and alkyne metathesis polymerization. With advances in catalyst development, polymer materials with various functional groups have been developed over recent years via metathesis polymerization.

In related arts, organic metal catalysts have been used for metathesis polymerization. Monomers with poly functional groups, however, are apt to perform multi-reaction in metathesis polymerization with organic metal catalysts. So the use of metathesis polymerization of monomers with poly functional groups has been limited.

Grubbs et. al. reported that the ring-opening metathesis polymerization (ROMP) of cyclo-olefin with Ru catalyst (($Cl_2Ru(CHPh)[PC_6H_{11}]_3)_2$) exhibits high performance. More particularly, the polymerization of the monomers with functional groups can be achieved with the catalyst because of the combined compound's stability in atmosphere. In addition, such metathesis polymerization resulted in polymers showing high polymerizing rates and large molecular weights, generally associated with living polymerization.

Hence, more research on ROMP of cyclo-olefin derivatives to improve catalyst reactivity soon followed. The research mainly also focused on the development of side-chain-type liquid crystals, triblock copolymers synthesized by two-step methods, polymers with various functional groups and polymers having cross-linkable functional groups present in the side chain thereof, etc. The introduction of functional groups improved the optical characteristics and biochemical activity of the polymer.

In addition, ever since nanotechnology and nanomaterials have been researched, compounds containing specific structures (such as amphiphilic compounds) have been prepared by ROMP. For example, the forming of compounds containing carbon-carbon double bonds by olefin ROMP.

In recent years, the ROMP of cycloolefin and metathesis polymerization of non-cyclodiolefin has become very important in polymer synthesis. The preparation of novel functional polymers form norbornene-type monomer is carried out by ROMP.

Polymers with specific functional groups have grown in importance as they exhibit optoelectronic characteristics, biological activity, and nanomaterial properties. Meanwhile, the characteristic of polymer material depends on structure, degree of polymerization, molecular weight, and distribution of molecular weight thereof.

Therefore, the invention provides norbornene monomers containing a fluorene group and polymer material thereof, which may further be utilized to prepare specific materials for industrial purposes.

BRIEF SUMMARY OF THE INVENTION

The norbornene compounds with fluorene groups of the invention are prepared by Diels-Alder reaction. After obtaining norbornene compounds with fluorene groups, novel polymers were further prepared by ring-opening metathesis polymerization (ROMP) of said compounds. Particularly, the molecular weight and molecular weight distribution of the polymer with side chains of fluorene group are modified by adjusting the molarity ratio of the norbornene compound and the catalyst.

The first aspect of the invention provide a norbornene compound with fluorene groups, which comprises a structures represented by formula (I),

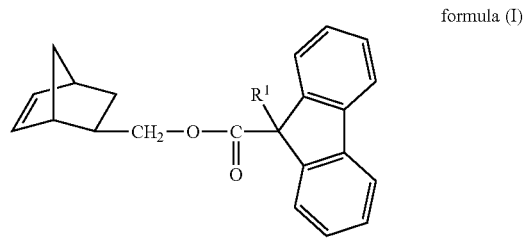

formula (I)

wherein, $R^1$ is H, $CH_3$, $C_2H_5$, $C_3H_7$, $C_4H_9$, $OCH_3$, $OC_2H_5$, $OC_3H_7$, or $OC_4H_9$.

The secondsond aspect of the invention provide a polymer with side chains of fluorene groups, which comprises a structures represented by formula (II),

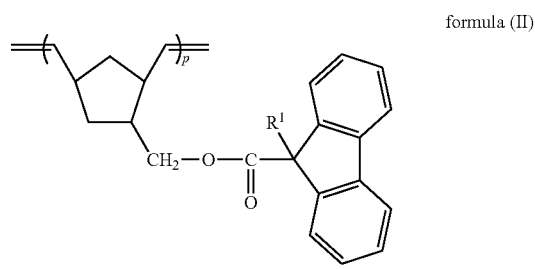

formula (II)

wherein $R^1$ is H, $CH_3$, $C_2H_5$, $C_3H_7$, $C_4H_9$, $OCH_3$, $OC_2H_5$, $OC_3H_7$, or $OC_4H_9$; and p is an integer between 2 to 1000.

The third aspect of the invention provide a norbornene block copolymer with carbazole groups and fluorene groups, which comprises a structures represented by formula (III),

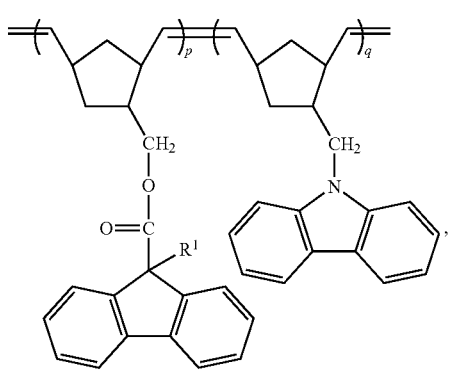

formula (III)

wherein, $R^1$ is H, $CH_3$, $C_2H_5$, $C_3H_7$, $C_4H_9$, $OCH_3$, $OC_2H_5$, $OC_3H_7$, or $OC_4H_9$;

p is an integer between 2 to 1000; and q is an integer between 1 to 100.

The fourth aspect of the invention provide a norbornene cross-linking polymer with fluorene groups, which comprises a structures represented by formula (IV),

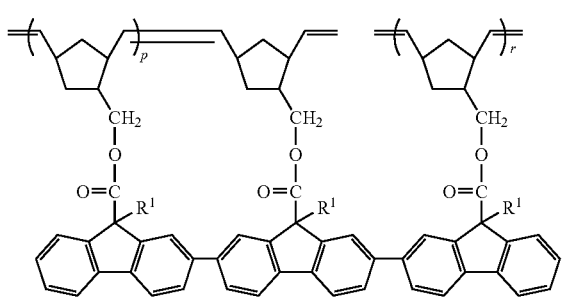

formula (IV)

wherein, $R^1$ is H, $CH_3$, $C_2H_5$, $C_3H_7$, $C_4H_9$, $OCH_3$, $OC_2H_5$, $OC_3H_7$, or $OC_4H_9$;

p is an integer between 2 to 1000; and r is an integer between 1 to 1000.

The fifth aspect of the invention provide a method for preparing polymer with side chains of fluorene groups, comprising:

polymerizing a norbornene compound with fluorene groups, comprising a structures represented by formula (I),

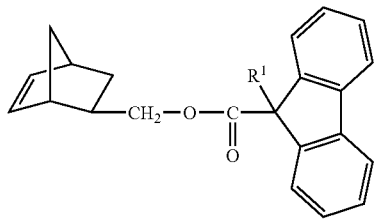

formula (I)

in the presence of $Cl_2Ru(CHPh)([PC_6H_{11}]_3)_2$ as a catalyst for preparing the polymer with side chains of fluorene groups comprising a structures represented by formula (II),

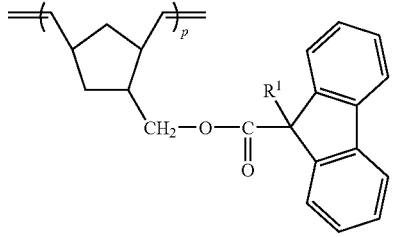

formula (II)

wherein, $R^1$ is H, $CH_3$, $C_2H_5$, $C_3H_7$, $C_4H_9$, $OCH_3$, $OC_2H_5$, $OC_3H_7$, or $OC_4H_9$; and p is an integer between 2 to 1000.

The sixth aspect of the invention provide a method for preparing norbornene block copolymer with carbazole groups and fluorene groups, comprising:

polymerizing a polymer with side chains of fluorene groups represented by formula (II),

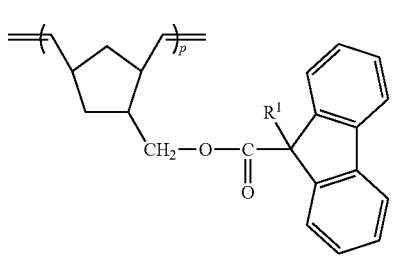

formula (II)

with a compound represented by formula (V), of:

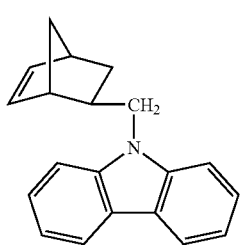

formula (V)

in the presence of $Cl_2Ru(CHPh)([PC_6H_{11}]_3)_2$ as a catalyst for preparing the norbornene block copolymer with carbazole groups and fluorene groups comprising a structures represented by formula (III),

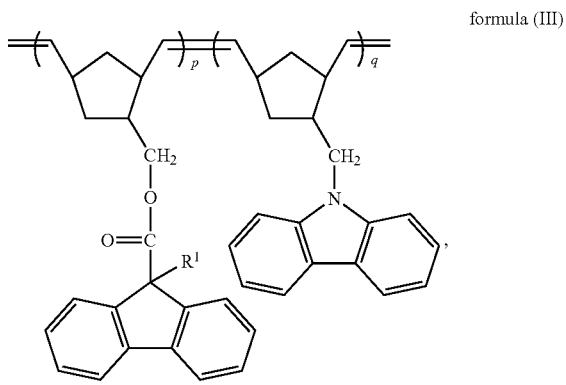

formula (III)

wherein, $R^1$ is H, $CH_3$, $C_2H_5$, $C_3H_7$, $C_4H_9$, $OCH_3$, $OC_2H_5$, $OC_3H_7$, or $OC_4H_9$;
p is an integer between 2 to 1000; and
q is an integer between 1 to 100.

The seventh aspect of the invention provides a method for preparing norbornene cross-linking polymer with fluorene groups, comprising:

polymerizing a polymer with side chains of fluorene groups represented by formula (II),

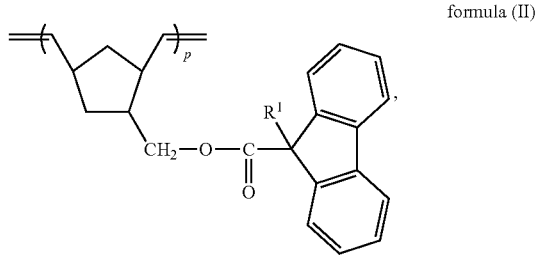

formula (II)

norbornene compound with fluorene groups represented by formula (I),

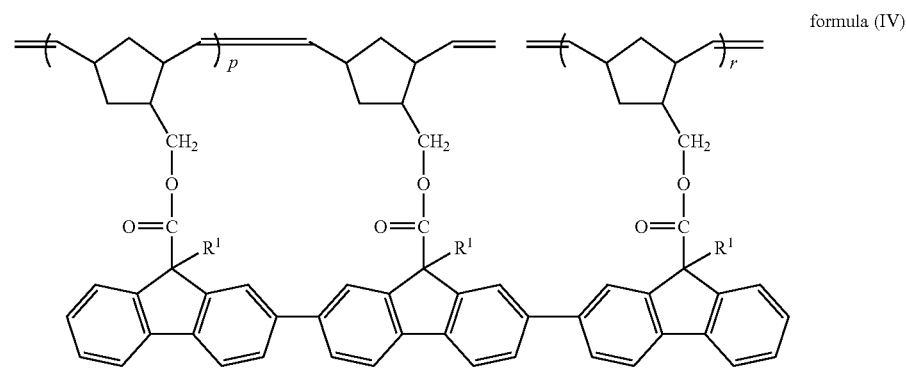

formula (I)

in the presence of $FeCl_3$ as a catalyst for preparing the norbornene cross-linking polymer with fluorene groups, which comprises a structures represented by formula (IV), formula (IV)

wherein, $R^1$ is H, $CH_3$, $C_2H_5$, $C_3H_7$, $C_4H_9$, $OCH_3$, $OC_2H_5$, $OC_3H_7$, or $OC_4H_9$;
p is an integer between 2 to 1000; and
r is an integer between 1 to 1000.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

Figure 1:
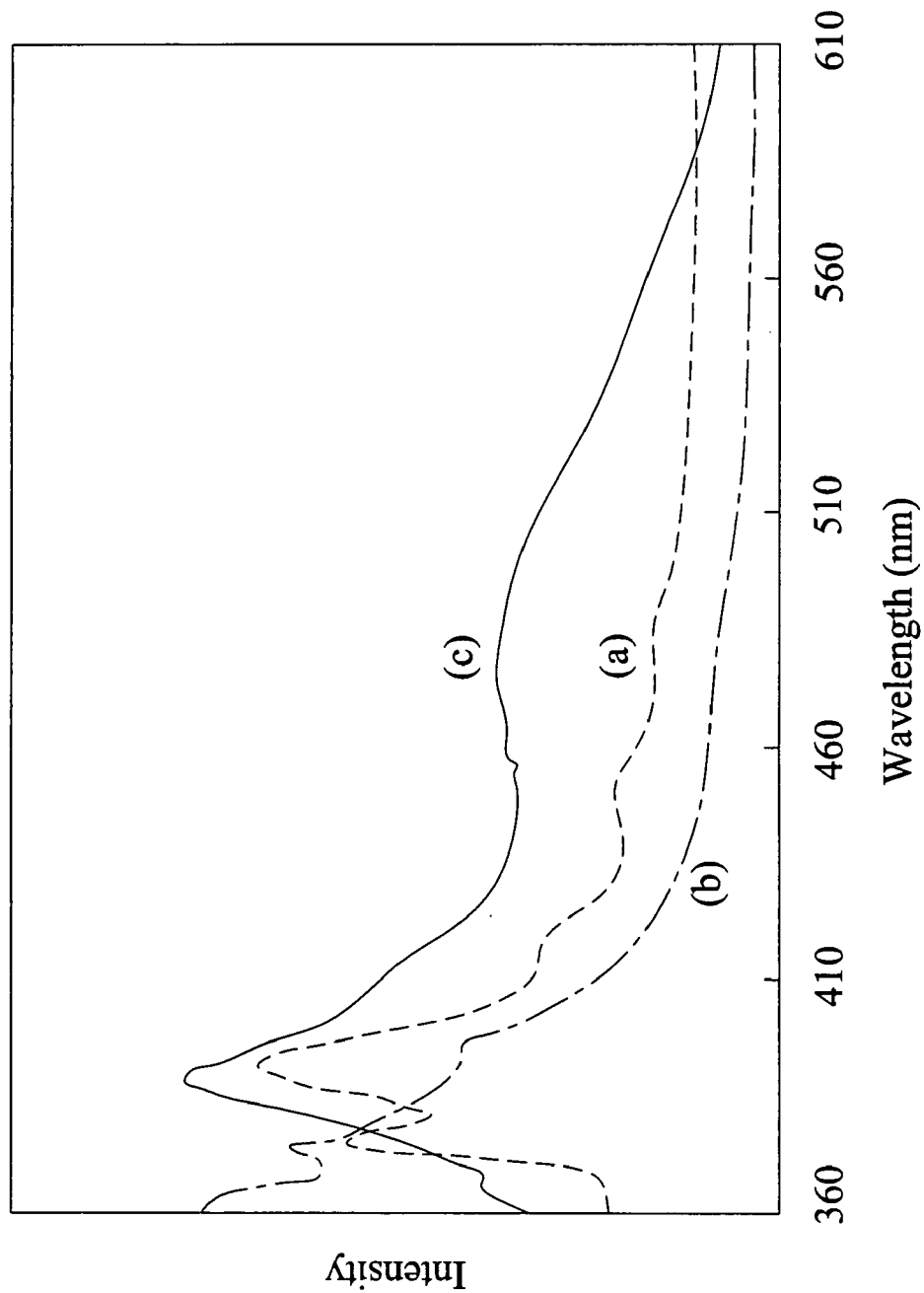
FIG. 1 shows fluorescence spectrograms of products of Examples 1, 2, and 6 of the invention.

The norbornene compounds with fluorene groups of the invention are prepared by Diels-Alder reaction. Novel polymers with narrow molecular weight distribution can be further prepared by ring-opening metathesis polymerization (ROMP) of said monomers.

It was difficult to design compounds which are polymerized by ring-opening metathesis polymerization. Further, exo isomers of norbornene showed more activity than endo isomers of norbornene. The norbornene compounds with fluorene groups can be used in laser technology and serve as fluorescent materials. The embodiment of the invention further provides a norbornene compound "exo-5-(fluorine carboxyl methyl) bicycle [2.2.1]hept-2-ene (exo-f) and polymers thereof", which can be applied in various industrial fields.

The reactive conditions for the metathesis polymerization of the present invention include:

(1) Metathesis Catalysts:

These catalysts are tungsten and molybdenum metathesis catalysts, including their halides, oxyhalides or oxides, for example, tungsten hexachloride, tungsten oxychloride, tungsten tetrachloride, molybdenum pentachloride, or molybdenum oxide acetyl acetocarboxylate. Ruthenium metathesis catalysts may also be used in the invention, preferably $Cl_2Ru(CHPh)([PC_6H_{11}]_3)_2$.

(2) Solvents:

The ring-opening metathesis polymerization of the present invention may be performed without solvents, but the reaction were usually carried out in inert organic solvent.

The preferable organic solvents used were hydrocarbon solvents. More specifically, cyclohydrocarbon solvents which completely dissolve ring-opened polymers. For example, aromatic hydrocarbon such as benzene, ethyl benzene, toluene or xylene; aliphatic hydrocarbon such as n-pentane, hexane or heptane; aliphatic cyclohydrocarbon such as cyclopentane, cyclohexane, methyl cyclohexane or dimethyl cyclohexane; halo hydrocarbon such as methylene chloride, ethylene chloride, dichloroethene, tetrachloroethane, chloroform, dichlorobenzene or trichlorobenzene; or the mixture of said solvents. In addition, the ratio of solvent to monomers typically ranged from 1:1 to 20:1, preferably 2:1 to 10:1.

(3) Temperature:

The temperature range for ring-opening metathesis polymerization was not limited, usually between −20~100° C., preferably between 0~100° C.

Ring-opened Polymers

The number-average molecular weight (Mn) of the ring-opening metathesis polymers and their co-polymers was 1000 to 60,000, and molecular weight distribution (Polydispersity index, PDI=Mw/Mn, i.e., the molecular weight distribution of polymerization) of the polymers and co-polymers was below 1.1. The ring-opened metathesis polymers can be further hydrogenated to form optic polymer materials. The molecular weight and polydispersity were determined by gel permeation chromatography (GPC). Tetrahydrofuran was used as a solvent.

Several examples are used for illustrating the present invention, and the objects, skills and characters will thus be more apparent.

EXAMPLE 1

Synthesis of norbornene monomer with terminal fluorene groups (exo-f)

25 ml of cyclopentadiene, 30.1 ml of methyl acrylate, and 30 ml of dichloromethane were mixed and heated to reflux for 24 hours. The result was added into 5.3 g of Na (dissolved in 80 ml methanol) for 4 hours. Next, the methanol was removed and the remains were dissolved in 50 ml water and heated to reflux, resulting in forcing of the methyl acrylate group to be altered to an acidic group. After acidifying by $H_2SO_4$, extraction by ether, and drying by $MgSO_4$, the result was added into 28.8 g sodium bicarbonate (dissolved in 460 ml water) to separate acidified isomers therefrom.

Next, 25.5 g of iodine, 53.2 g potassium iodide, and 150 ml of water were mixed and added into the above solution. After removing the endo isomer by water extraction, the result was further acidified, crystallized by pentane at −78° C. to obtain exo-b as a yellow crystal.

Next, 3.5 g of exo-b was dissolved in 150 ml ether for 4 hours, and 1.45 g of lithium aluminum hydride (dissolved in 25 ml of ether) was added into the above solution at room temperature for 9 hours and heated to reflux for 45 minutes. After cooling, 15 ml HCl (dissolved in water, 20%) was added. After extraction and drying by calcium sulfate, exo-5-(hydroxyl methyl) bicyclo[2.2.1]hept-2-ene (exo-e) was obtained. Next, exo-e was reacted with 9H-fluorene-9-carboxylic acid to thereby obtain norbornene monomer with terminal fluorene groups (exo-f) with a melt point of 44-45° C.

The reaction according to Example 1 is shown in reaction formula (I):

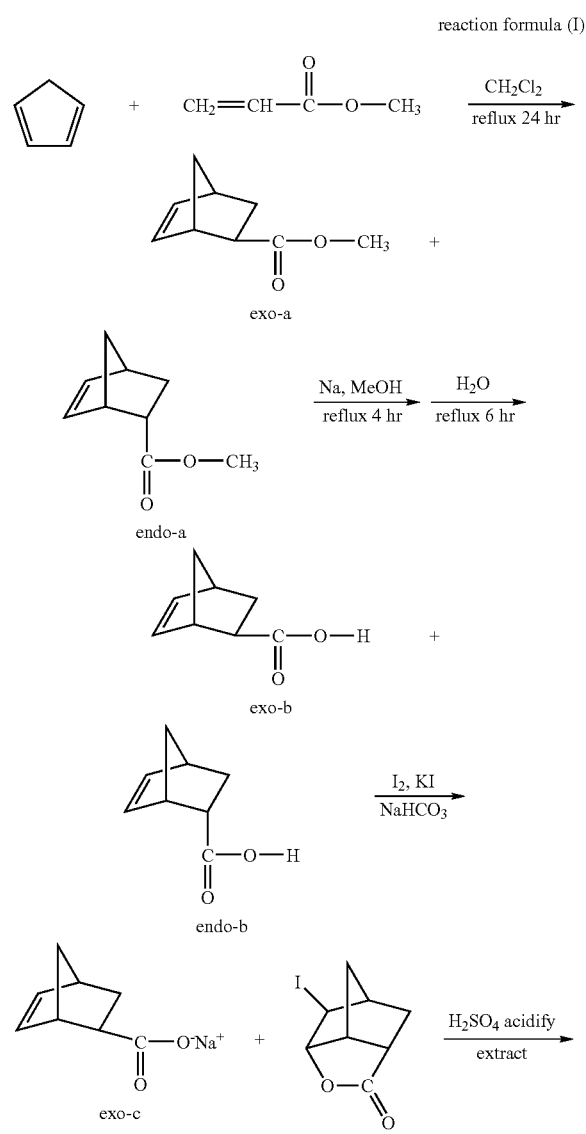

reaction formula (I)

-continued

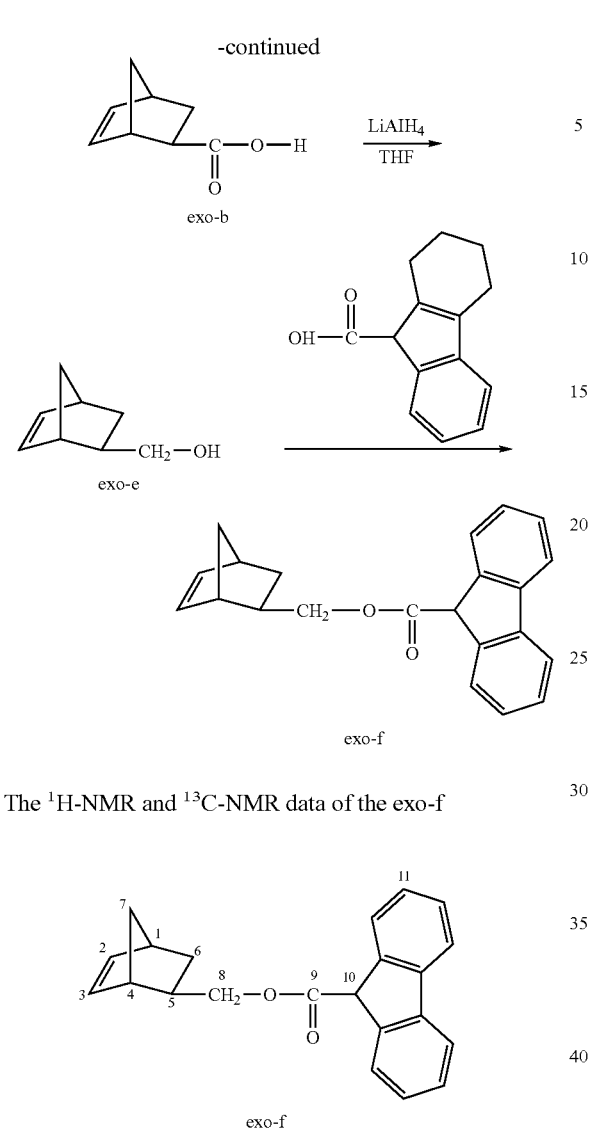

exo-b exo-e exo-f $(RuCl_2[C_{21}H_{26}N_2][CHC_6H_5]P(C_6H_{11})_3)$ (dissolved in 0.2 ml of THF) was added and argon was subsequently injected into reactor with a syringe.

After reacting at 35° C. for 90 seconds, 0.1 ml ethyl vinyl ether was added into the bottle to terminate the reaction. The resulting solution was added to 500 ml of methyl alcohol and the mixture was dissolved in 10 ml of methylene chloride and extracted with 500 methanol three times, thereby obtaining the norbornene monomer polymer with side chains of fluorene groups.

The glass transition temperature (Tg) of the above norbornene polymer was 80° C. which was determined by differential scanning calorimeter (DSC). The exothermal peak for the glass transition temperature (Tg) of a conventional norbornene polymer was 35° C. Therefore, the norbornene polymer of the invention showed higher thermal stability than the conventional norbornene polymer.

The reaction according to Example 2 is shown in reaction formula (II):

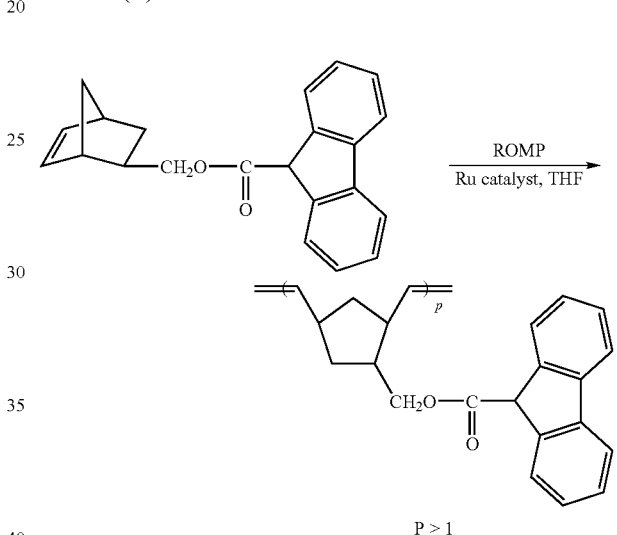

P > 1 wherein, p>1 reaction formula (II)

The $^1$H-NMR and $^{13}$C-NMR data of the exo-f

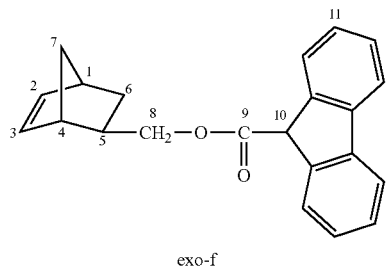

exo-f

The $^1$H-NMR and $^{13}$C-NMR data of the exo-f was shown below:

$^1$H-NMR(CDCl$_3$): δ/ppm=1.18-1.21 (H$_6$,H$_7$), 1.27-1.37 (H$_7$), 1.77-1.81 (H$_5$), 2.68 (H$_4$), 2.86 (H$_1$), 4.09-4.28 (H$_8$), 4.92 (H$_{10}$), 6.11 (H$_2$, H$_3$), 7.37-7.80 (H$_{11}$)

$^{13}$C-NMR(CDCl$_3$): δ/ppm=29.49 (C$_6$), 37.95 (C$_5$), 41.52 (C$_1$), 43.58 (C$_4$), 44.92 (C$_7$), 53.47 (C$_{10}$), 69.34 (C$_8$), 136.21 (C$_3$), 137.99 (C$_2$), 119.94, 125.53, 127.21, 127.99, 140.67, 141.36, 170.75 (C$_9$)

Referring to FIG. 1, curve (a) represented the fluorescence spectrograms of products of Example 1. Accordingly, the fluorescence spectrograms of exo-f has a strong peak at 391 nm and a smooth peak at 375~420 nm.

EXAMPLE 2

Synthesis of Norbornene Monomer Polymer with Side Chains of Fluorene Groups

First, exo-f was subjected to a vacuum distillation at 115° C./4 mmHg to obtain purified exo-f monomer. Next, 0.911 mmol of exo-f was added into 3 ml of THF and degassed fourfold via freeze-pump-thaw cycle. 75 mg of Ru catalyst The $^1$H-NMR and $^{13}$C-NMR data of the norbornene monomer

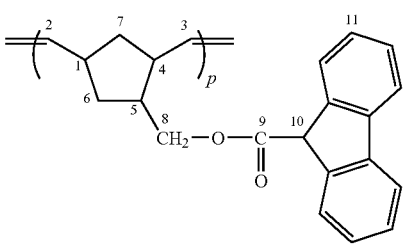

was shown below:

$^1$H-NMR(CDCl$_3$): δ/ppm=1.14-2.71 (H$_1$, H$_4$, H$_5$, H$_6$, H$_7$), 3.75-4.13 (H$_8$), 4.85 (H$_{10}$), 5.10-5.27 (H$_2$, H$_3$), 7.26-7.73 (H$_{11}$)

$^{13}$C-NMR(CDCl$_3$): δ/ppm=29.85-46.27 (C$_1$, C$_4$, C$_5$, C$_6$, C$_7$), 53.56 (C$_{10}$), 69.90 (C$_8$), 131.37-132.79 (C$_3$, C$_2$), 120.02, 125.63, 127.29, 128.10, 140.72, 141.43 (C$_{11}$), 170.95 (C$_9$) (trans/cis: 85/15)

Referring to FIG. 1, curve (b) represented the fluorescence spectrograms of products of Example 2. Accordingly, the fluorescence spectrograms of the norbornene monomer had two main peaks at 365 nm nm and 375 nm resulting from different agglutination properties.

EXAMPLE 3

Method for modifying the molecular weight of the norbornene polymer by adjusting [M]/[I]

Figure 2:
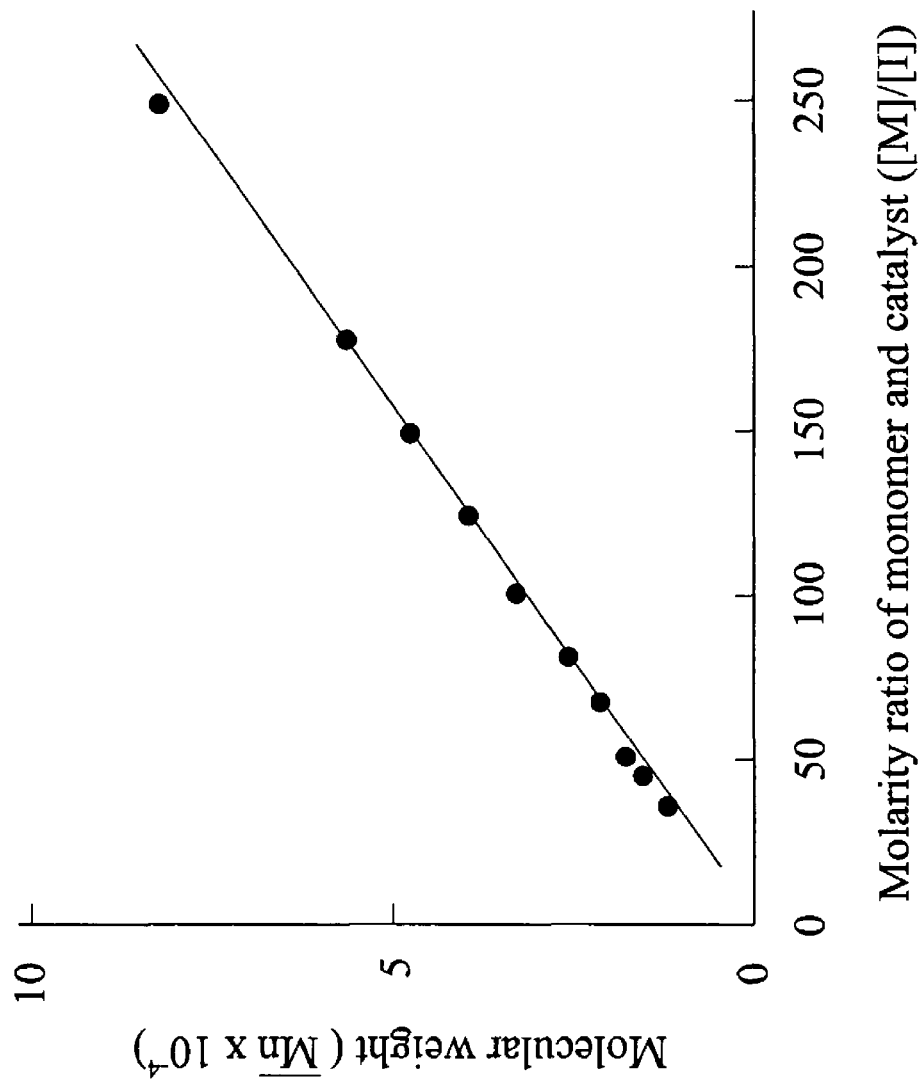
FIG. 2 shows a graph plotting molarity ratio of monomer and Ru catalyst ([M]/[I]) against molecular weight of norbornene polymer as disclosed in Example 3.

Example 3 was performed as Example 2 except for substitution of the molarity ratio of NBMGE and Ru catalyst ([M]/[I]) 250 to 40. The molecular weight of the obtained polymer was measured by gel permeation chromatography (GPC) analysis, as shown in FIG. 2. Accordingly, it should be noted that the molecular weight and molecular weight distribution of the polymer with side chains of fluorene group can be modified by adjusting the molarity ratio of the norbornene compound and the catalyst.

Figure 3:
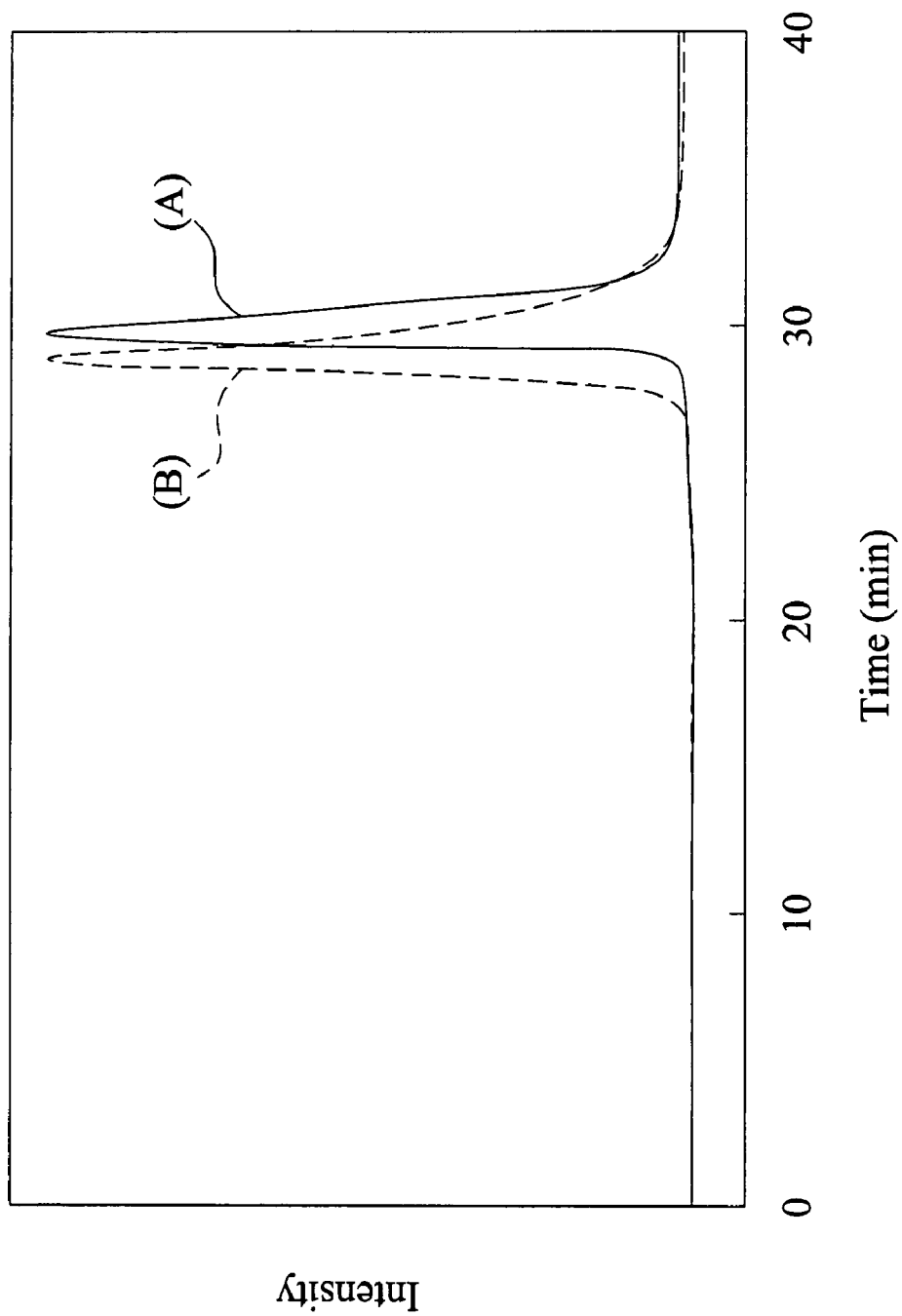
FIG. 3 shows the measurement of molecular weight of products of Examples 3 and 5 of the invention by GPC.

Referring to FIG. 3, the curve (A) illustrated the measurement of the molecular weight of the norbornene polymer with side chains of fluorene group ([M]/[I])=125), and the norbornene polymer has a PDI value of 1.06. It should be noted that the polymerization of Example 3, employing $RUCl_2[C_{21}H_{26}N_2][CHC_6H_5]P(C_6H_{11})_3$, has a reaction time of 90 seconds for achieving living polymerization. When the molarity ratio of monomer and catalyst([M]/[I]) increased, the molecular weight of the norbornene polymer also increased linearly. Further, the polymerization has a yield of 99%, and the obtained norbornene polymer had a molecular weight near the theoretical molecular weight and a PDI value of 1.05 to 1.1. The structures of the polymer were determined by $^1$H-NMR and $^{13}$C-NMR. For $^1$H-NMR, a strong peak δ5.5~6,0 ppm (double bond of norbornene) was diminished during polymerization, and a resonance of double bond of linear chain of norbornene polymer was observed at 5.1-5.2 ppm (trans/cis=85/15). According to data of NMR, it shown that the norbornene monomer was consumed during 90 seconds. Therefore, the norbornene monomer of the invention exhibits living polymerization characteristics, and can further prepare specific norbornene block copolymer material.

EXAMPLE 4

Method for modifying the molecular weight of the norbornene polymer by batch addition First, 35 equivalent of exo-f was added into 3 ml of THF and degassed Fourfold via freeze-pump-thaw cycle. 1 equivalent of Ru catalyst ($RuCl_2[C_{21}H_{26}N_2][CHC_6H_5]P(C_6H_{11})_3$) (dissolved in 0.2 ml of THF) was added into the reactor. After reacting at 35° C. for 90 seconds, the product was measured and had a molecular weight of $1.14 \times 10^4$ (theoretical molecular weight of $1.10 \times 10^4$ ([M]/[I]=35)). Next, 35 equivalent of exo-f was further added into the reactor. After reacting at 35° C. for 90 seconds, the product in the reactor was measured and had a molecular weight of $2.55 \times 10^4$ and a PDI value of 1.10.

Accordingly, the invention can prepare norbornene polymers with various molecular weights and narrow molecular weight distributions in a short period of time.

COMPARATIVE EXAMPLES 1-9

Referring to Table. 1, comparative examples 1-9 discloses conventional ring-opening-metathesis polymerizations for polymerizing norbornene compound. The monomers used in comparative examples 1-6 were further polymerized with Ru catalyst (Ru-1, the catalyst disclosed by the invention) via ring-opening-metathesis polymerization. However, the above polymerizations have reaction time of 25 min to 5 hr for completely polymerizing to achieve theoretical molecular weight. In comparative example 7, an expensive catalyst (Ru-2) was used to reduce the reaction time of ring-opening-metathesis polymerization, but the polymerization still had a reaction time of 4 hr. In comparative example 8, a so-called "Super-Grubbscatalyst" (Ru-3, with N-hetero-cyclic carbon) was used. However, the obtained polymer of comparative example 8 had a wider molecular weight distribution and a reaction time of more than 20 hours to achieve living polymerization. In order to reduce the reaction time of ring-opening-metathesis polymerization, comparative example 9 disclosed a polymerization with Ru-4, but the polymerization still had a reaction time of about 30 min. In comparative with comparative examples 1-9, the embodiments of the invention, employing the specific norbornene monomers and Ru-1, had reaction time of about 90 seconds for achieving living polymerization.

TABLE 1

Comparative Examples 1~9

| | Monomer | [M]/[I] | Time | Temp. | Yield | PDI | Mw ($10^4$) |
|---|---|---|---|---|---|---|---|
| The Invention | 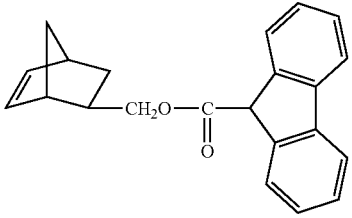 | 125 (Ru-1) | 90 secs | 35 | 99 | 1.06 | 3.9 |
| Comparative Example 1 |  | 50 (Ru-1) | 45 mins | 25 | 99 | 1.15 | 1.09 |

TABLE 1-continued

Comparative Examples 1~9

| | Monomer | [M]/[I] | Time | Temp. | Yield | PDI | Mw (10⁴) |
|---|---|---|---|---|---|---|---|
| Comparative Example 2 | norbornene-C(O)-NHCH₂COOCH₃ | 36 (Ru-1) | 35 mins | 25 | 99 | 1.12 | 0.46 |
| Comparative Example 3 | norbornene-C(O)-OCH₂O-pyridine-2,6-bis(NH-C(O)CH₂CH₃) | 115 (Ru-1) | 120 mins | 25 | 100 | 1.06 | 3.76 |
| Comparative Example 4 | norbornene-C(O)-OCH₂O-C₆H₃(SPh)₂Pd-Cl | 20 (Ru-1) | 25 mins | 25 | 100 | 1.25 | 4.99 |
| Comparative Example 5 | tetracyclic-C(O)-NHCH₂COOCH₃ | 100 (Ru-1) | <5 mins | 25 | 99 | 29 | 0.1 |
| Comparative Example 6 | norbornene-2,3-bis(C(O)OCH₂CH₃) | 300 (Ru-1) | 5 hrs | 40 | 98 | 1.06 | 7.58 |
| Comparative Example 7 | norbornene-dicarboximide-NCOOCH₃ | 100 (Ru-2) | 4 hrs | 30 | 98 | 1.05 | 3.26 |
| Comparative Example 8 | norbornene-2,3-bis(C(O)OCH₂CH₃) | 100 (Ru-3) | 120 secs | 23 | 99 | 1.40 | 1.60 |

TABLE 1-continued

Comparative Examples 1~9

| Monomer | | [M]/[I] | Time | Temp. | Yield | PDI | Mw (10⁴) |
|---|---|---|---|---|---|---|---|
| Comparative Example 9 | 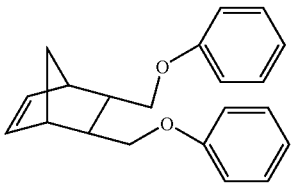 | 200 (Ru-4) | 30 mins | 23 | 92 | 1.04 | 6.09 |

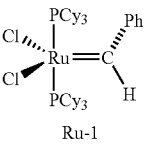

Ru-1

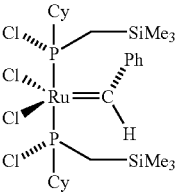

Ru-2

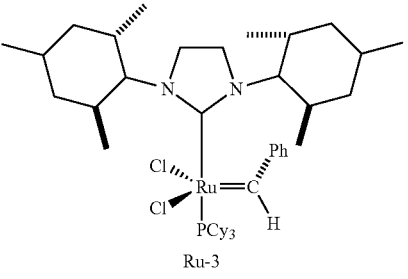

Ru-3

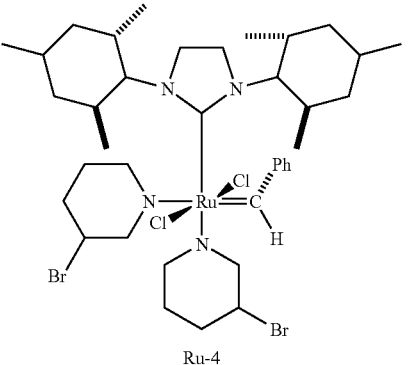

Ru-4

EXAMPLE 5

Synthesis of norbornene block copolymer with carbazole groups and fluorene groups First, exo-f was dissolved in THF and degassed fourfold via freeze-pump-thaw cycle. Next, Ru catalyst (RuCl$_2$[C$_{21}$H$_{26}$N$_2$][CHC$_6$H$_5$]P(C$_6$H$_{11}$)$_3$) (dissolved in 0.2 ml of THF) was added into the reactor, wherein the molarity ratio of the norbornene compound and the catalyst ([M]/[I]) was 125. After reacting at 35° C. for 90 seconds, poly-exo-f was obtained, with a molecular weight of 3.90×10⁴ and a PDI value of 1.06 (theoretical molecular weight of 3.96×10⁴).

Next, norbornene monomer with carbazole groups ([M]/[I])=50) was added into the reactor with poly-exo-f. After stirring for 2 hours, 0.2 ml ethyl vinyl ether was added into the bottle to terminate the reaction. The resulting solution was added to 500 ml of methyl alcohol and the mixture was dissolved in 10 ml of methylene chloride and extracted with 500 methanol three times, thereby obtaining the norbornene block copolymer with carbazole groups and fluorene groups (Poly(exo-f)-b-(NBCbz)). Poly(exo-f)-b-(NBCbz) showed a molecular weight of $5.21\times10^4$ and a PDI value of 1.21 (theoretical molecular weight of $5,23\times10^4$). Referring to FIG. 3, the curve (B) illustrated the measurement of the molecular weight of the norbornene block copolymer with carbazole groups and fluorene groups.

The reaction according to Example 5 is shown in reaction formula (III)

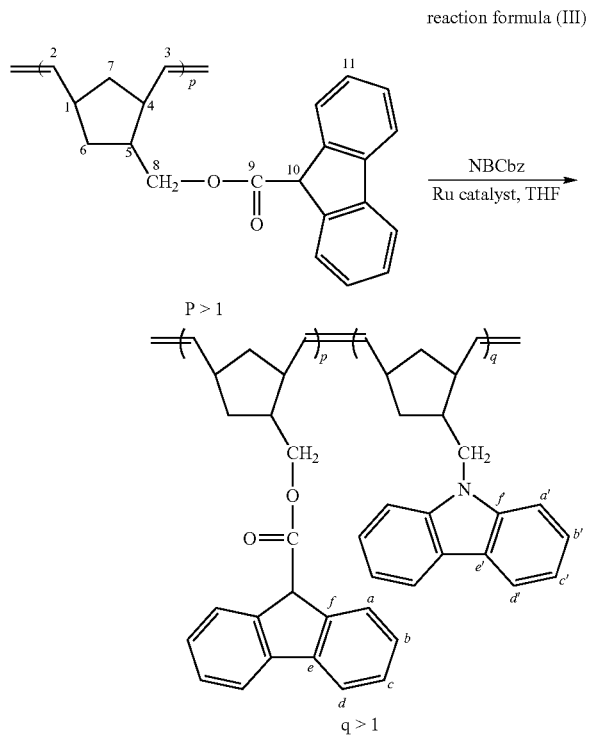

reaction formula (III)

The $^1$H-NMR and $^{13}$C-NMR data of poly-exo-f shows fluorene groups signals at δ/ppm: 7.26~7.73 ($H_a$-$H_d$) ($^1$HNMR) and δ/ppm: 118.63, 125.60, 127.28, 128.31 ($C_a$~$C_d$) and 140.38, 140.37 ($C_e$~$C_f$) ($^{13}$CNMR). Further, after forming the norbornene block copolymer with carbazole groups and fluorene groups, the $^1$H-NMR and $^{13}$C-NMR data of the norbornene block copolymer shows carbazole groups signals at δ/ppm: 8.11, 7.26~7.73 ($^1$H NMR) and δ/ppm 109.79, 118.54, 120.28, 125.43 ($C_{a'}$~$C_{d'}$) and 112.81, 138.49 ($C_{e'}$, $C_{f'}$).

EXAMPLE 6

Synthesis of norbornene cross-linking polymer with fluorene groups

The norbornene polymer with side chains of fluorene groups (poly(exo-f)) can be further oxidized via $FeCl_3$ to form π-conjugatd derivatives (bonded in the 2,7-location of fluorene)

First, 0.1 g of poly-exo-f (1 equivalent) was dissolved in 10 ml of Chloroform, and 5 equivalent of iron (III) chloride was added into the above solution, and the color of the solution changed to a brown color. After stirring for 4 hr, excess methanol was added into the mixture to obtain norbornene cross-linking polymer with fluorene groups.

Referring to FIG. 1, curve (c) represented the fluorescence spectrograms of the norbornene cross-linking polymer with fluorene groups of Example 6. Accordingly, the fluorescence spectrograms of norbornene cross-linking polymer with fluorene groups showed a strong peak at 350 nm caused by 2,7-fluorene.

The glass transition temperature (Tg) of the above norbornene cross-linking polymer was 161° C., and the glass transition temperature of poly-exo-f was 80° C.

The reaction according to Example 6 was shown in reaction formula (IV):

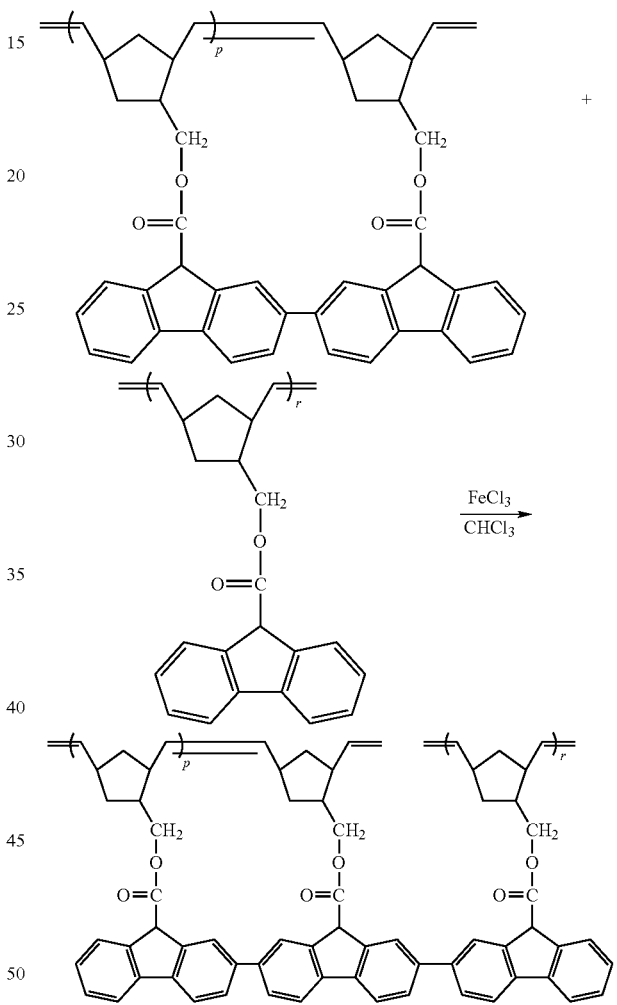

wherein, p>1 and r>1 reaction formula (IV)

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A norbornene compound with fluorene groups, which comprises a structure represented by formula (I), of:

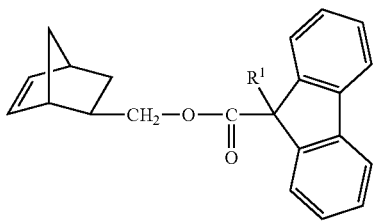

wherein
R$^1$ is H, CH$_3$, C$_2$H$_5$, C$_3$H$_7$, C$_4$H$_9$, OCH$_3$, OC$_2$H$_5$, OC$_3$H$_7$, or OC$_4$H$_9$.

2. A polymer, which comprises a structure represented by formula (II), of:

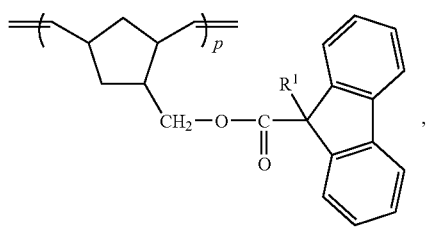

formula (III), of:

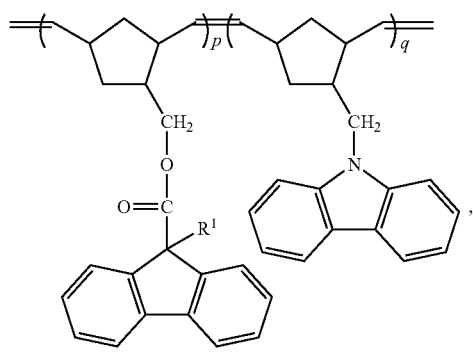

or formula (IV), of:

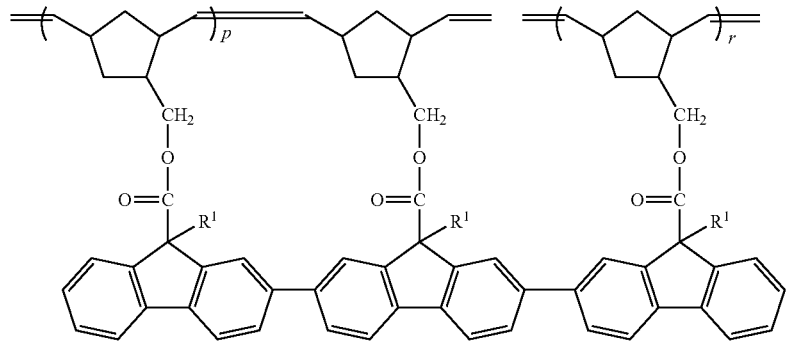

wherein
R$^1$ is H, CH$_3$, C$_2$H$_5$, C$_3$H$_7$, C$_4$H$_9$, OCH$_3$, OC$_2$H$_5$, OC$_3$H$_7$, or OC$_4$H$_9$;
p is an integer between 2 to 1000;
q is an integer between 1 to 100; and
r is an integer between 1 to 1000.

3. A method for preparing a polymer with side chains of fluorene groups, comprising:
polymerizing a norbornene compound with fluorene groups, comprising a structure represented by formula (I), of

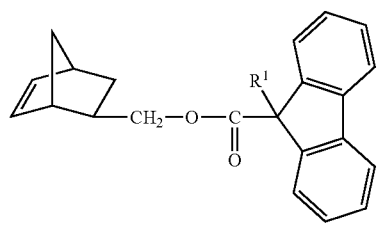

in the presence of Cl$_2$Ru(CHPh)([PC$_6$H$_{11}$]$_3$)$_2$ as a catalyst for preparing the polymer with side chains of fluorene groups, which polymer comprises a structure represented by formula (II), of:

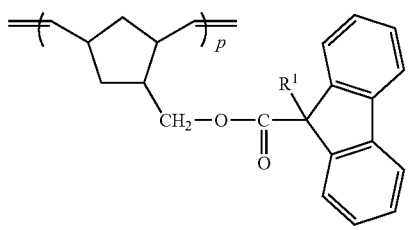

wherein
R$^1$ is H, CH$_3$, C$_2$H$_5$, C$_3$H$_7$, C$_4$H$_9$, OCH$_3$, OC$_2$H$_5$, OC$_3$H$_7$, or OC$_4$H$_9$; and
p is an integer between 2 to 1000.

4. The method as claimed in the claim 3, wherein the molecular weight and molecular weight distribution of the polymer with side chains of fluorene group are modified by adjusting the molarity ratio of the norbornene compound and the catalyst.

5. A method for preparing a norbornene block copolymer with carbazole groups and fluorene groups, comprising:
polymerizing a polymer with side chains of fluorene groups represented by formula (II), of:

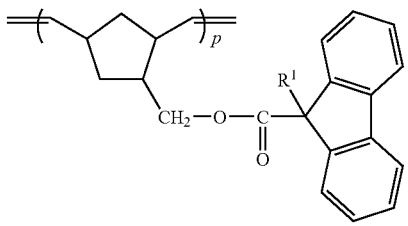

with a compound represented by formula (V), of:

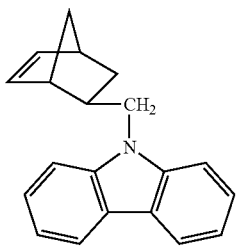

in the presence of $Cl_2Ru(CHPh)([PC_6H_{11}]_3)_2$ as a catalyst for preparing the norbornene block copolymer with carbazole groups and fluorene groups comprising a structure represented by formula (III), of:

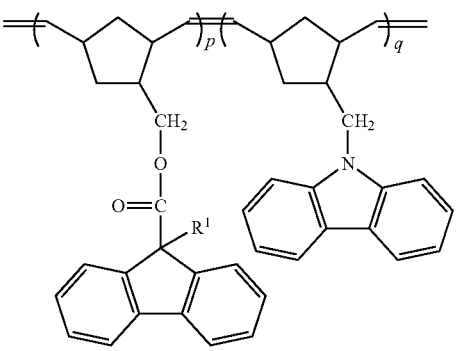

wherein
$R^1$ is H, $CH_3$, $C_2H_5$, $C_3H_7$, $C_4H_9$, $OCH_3$, $OC_2H_5$, $OC_3H_7$, or $OC_4H_9$;
p is an integer between 2 to 1000; and
q is an integer between 1 to 100.

* * * * *